United States Patent
Suriano et al.

(10) Patent No.: US 11,701,314 B2
(45) Date of Patent: Jul. 18, 2023

(54) PROCESSES AND METHODS

(71) Applicant: Colgate-Palmolive Company, New York, NY (US)

(72) Inventors: David Suriano, Edison, NJ (US); Diana Henao, Dover, NJ (US); Yun Xu, Langhorne, PA (US)

(73) Assignee: Colgate-Palmolive Company, New York, NY (US)

( * ) Notice: Subject to any disclaimer, the term of this patent is extended or adjusted under 35 U.S.C. 154(b) by 55 days.

(21) Appl. No.: 17/388,562

(22) Filed: Jul. 29, 2021

(65) Prior Publication Data

US 2022/0031586 A1 Feb. 3, 2022

Related U.S. Application Data

(60) Provisional application No. 63/059,674, filed on Jul. 31, 2020.

(51) Int. Cl.
*A61K 8/27* (2006.01)
*A61K 8/46* (2006.01)
*A61Q 11/00* (2006.01)

(52) U.S. Cl.
CPC ............... *A61K 8/27* (2013.01); *A61K 8/463* (2013.01); *A61Q 11/00* (2013.01); *A61K 2800/596* (2013.01); *A61K 2800/805* (2013.01); *A61K 2800/87* (2013.01); *A61K 2800/92* (2013.01)

(58) Field of Classification Search
CPC . A61K 8/81; A61K 8/27; A61Q 11/00; B08B 7/00
USPC ...................... 134/42; 424/49, 401
See application file for complete search history.

(56) References Cited

U.S. PATENT DOCUMENTS

| | | | |
|---|---|---|---|
| 4,575,457 A | 3/1986 | Mazarin | |
| 9,486,396 B2 | 11/2016 | Jaracz et al. | |
| 10,058,493 B2 | 8/2018 | Manus et al. | |
| 10,342,750 B2 | 7/2019 | Prencipe et al. | |
| 10,441,517 B2 | 10/2019 | Prencipe et al. | |
| 10,617,620 B2 | 4/2020 | Prencipe et al. | |
| 2007/0044824 A1* | 3/2007 | Capeci | B01F 35/2209 134/42 |
| 2009/0202454 A1 | 8/2009 | Mello et al. | |
| 2009/0202455 A1 | 8/2009 | Kohli et al. | |
| 2010/0055052 A1* | 3/2010 | Berta | G05D 11/133 424/49 |
| 2013/0071456 A1 | 3/2013 | Fruge et al. | |
| 2015/0313813 A1 | 11/2015 | Rege et al. | |
| 2016/0331670 A1* | 11/2016 | Prencipe | A61K 8/347 |
| 2018/0015016 A1 | 1/2018 | Huang et al. | |
| 2018/0021234 A1 | 1/2018 | Prencipe et al. | |
| 2018/0153778 A1 | 6/2018 | Potnis et al. | |
| 2019/0151209 A1 | 5/2019 | Shi et al. | |
| 2020/0197267 A1 | 6/2020 | Evans et al. | |

FOREIGN PATENT DOCUMENTS

| | | |
|---|---|---|
| CN | 109674875 | 4/2019 |
| WO | WO 2011/162755 | 12/2011 |

OTHER PUBLICATIONS

International Search Report and the Written Opinion of the International Searching Authority issued in International Application PCT/US2021/043649 dated Nov. 26, 2021.

* cited by examiner

*Primary Examiner* — Walter E Webb

(57) ABSTRACT

The disclosure is directed to processes and methods of reducing bloating and breakage of containers and packaging that house oral care compositions. Also contemplated are products and formulations that are produced or obtained from the processes and methods described herein.

19 Claims, No Drawings

PROCESSES AND METHODS

CROSS-REFERENCE TO RELATED APPLICATIONS

This application claims priority to and the benefit of U.S. Provisional Application No. 63/059,674, filed Jul. 31, 2020, the contents of which are hereby incorporated by reference in its entirety.

FIELD OF THE INVENTION

The disclosure is directed to processes and methods of reducing bloating and breakage of containers and packaging that house oral care compositions. Also contemplated are products and formulations that are produced or obtained from the processes and methods described herein.

BACKGROUND it is desirable to reduce instability of dentifrice formulations while in either short- or long-term storage. Instability during storage is due to the reactive ingredients having a tendency to react or decompose in the dentifrice vehicle when subjected to a storage environment of abnormally high temperatures. Due to such instability, the presence of the reactive ingredients causes expansion and bloating of the containers in which the dentifrice product is stored rendering the product unacceptable for consumer use. Expansion or bloating of containers can be costly to a manufacturer if the bloating leads to formulations that are ineffective, or containers which break or leak.

Because of the storage stability problems with dentifrices containing reactive ingredients such as bicarbonate compounds. Problems can also arise where the pH of a particular formula varies and can cause certain ingredients to react, i.e., causing various acid/base reactions which may result in gas building up well after tubes have been filed in manufacturing. Dentifrices containing such reactive components are sometimes constructed in a way that separates one or more ingredients until the point of use. Such dual packaging devices are costly to manufacture and attempts at simultaneous even delivery of the two separate dentifrice components from the dual compartmented device can be inconsistent.

There is therefore a need in the art for a dentifrice containing reactive ingredients, such as bicarbonate salts, where the dentifrice remains stable during storage for extended periods of time and can be stored without provision for costly physical separation of components.

BRIEF SUMMARY

In one aspect, the disclosure provides the surprising discovery that the addition of a pH adjusting agent, e.g., sodium carbonate (e.g., soda ash), at the early stages of the production of a process of dentifrice formulations containing a metal salt (e.g., zinc citrate), is believed to be successful in reducing bloating and bursting in tubes over long term storage. Without being bound by theory, the addition of a pH adjuster (e.g., sodium carbonate) at the early stages of formation of the premix can prevent or reduce generation of carbon dioxide in the final composition. Again, without being bound by theory, adding the pH adjuster in the premix can possibly neutralize the acid that is formed and results in a more efficient production process. In this aspect, and without being bound by theory, by adding the pH adjuster to the premix, one advantage is that the components do not need to first react, and then allow time for gas to dissipate. Moreover, the addition of a pH adjuster (e.g., sodium carbonate) is believed to create a stronger and more robust buffering system which allows a metal salt (e.g., zinc citrate) to remain stable in the formulation longer.

In one aspect, the process described herein is an improvement in that it minimizes bloating, and is believed to improve the stability of zinc citrate. Without being bound by theory, the process described herein allows zinc citrate to remain in the formulation and not decompose, for example by limiting the amount of carbonic acid that is generated. In this respect, the process described herein is particularly useful for chalk-based formulas, or chalk-based abrasives. As acid and chalk can combine to form carbon dioxide, minimizing the amount of carbonic acid has the effect of also reducing the amount of bloating.

The following description of embodiment(s) is merely exemplary in nature and is in no way intended to limit the invention, its application, or uses.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight relative to the total weight of the composition. The amounts given are based on the active weight of the material.

As is usual in the art, the compositions described herein are sometimes described in terms of their ingredients, notwithstanding that the ingredients may disassociate, associate or react in the formulation. Ions, for example, are commonly provided to a formulation in the form of a salt, which may dissolve and disassociate in aqueous solution. It is understood that the invention encompasses both the mixture of described ingredients and the product thus obtained.

The invention contemplates a Process (1.0) for producing an oral care composition comprising:
- a.) forming a first aqueous premix comprising water, a pH adjusting agent (e.g., sodium carbonate) and a zinc salt (e.g., zinc citrate);
- b.) forming a second premix comprising one or more humectants (e.g., glycerin and xanthan gum);
- c.) forming a third aqueous premix comprising water and an anionic surfactant (e.g., sodium lauryl sulfate);
- d.) transferring the second premix to a separate tank (e.g., gel tank);
- e.) transferring the first, second, and third premixes to a separate mixer or a mix tank;
- f.) homogenizing and forming the first, second, and third premixes into a final composition within the mixer or mix tank, wherein the final composition comprises all of the above premixes.

In a further aspect, the Process 1.0 comprises the following:
- 1.1 The Process of 1.0, wherein the pH adjusting agent is selected from the group consisting of: sodium bicarbonate, sodium carbonate, disodium hydrogen phosphate and sodium dihydrogen phosphate.
- 1.2 The Process of 1.0 or 1.1, wherein the pH adjusting agent is sodium carbonate.

1.3 The Process of any of 1.0-1.2, wherein the sodium carbonate is present in an amount from 0.1%-1% by weight of the final composition.
1.4 The Process of any of the preceding processes, wherein the sodium carbonate is present in an amount of about 0.25% by wt weight of the final composition.
1.5 The Process of any of the preceding processes, wherein the zinc salt is selected from zinc chloride, zinc lactate, zinc sulfate, zinc citrate and/or zinc oxide.
1.6 The Process of any of the preceding processes, wherein the zinc salt is zinc citrate.
1.7 The Process of any of the preceding processes, wherein the first aqueous premix is only transferred to the mixer or mix tank after an amount of time that is effective to ensure that the first aqueous premix does not contain any carbon dioxide gas. (e.g., at least 8 hours before transfer)
1.8 The Process of any of the preceding processes, wherein the first aqueous premix is formed at least 8 hours prior to being transferred to the mixer or mix tank.
1.9 The Process of any of the preceding processes, wherein the mixer or mix tank is heated to at least 130° F. prior to transfer of any of the premixes.
1.10 The Process of 1.9, wherein the mixer or mix tank is heated to 130° F.-180° F. prior to transfer of either the first or second premixes.
1.11 The Process of 1.10, wherein the mixer or mix tank is heated to 150° F.-170° F. prior to transfer of any of the premixes.
1.12 The Process of 1.11, wherein the mixer or mix tank is heated to about 160° F. (e.g., 160° F.) prior to transfer of any of the premixes.
1.13 The Process of any of the preceding processes, wherein the components in the mixer or mix tank are homogenized at a temperature of about 160° F.
1.14 The Process of any of the preceding processes, wherein an additional humectant (e.g., glycerin) is added to the second premix while it is in the tank (e.g., gel tank).
1.15 The Process of any of the preceding processes, wherein the process further comprises forming a third aqueous premix prior to the homogenization step.
1.16 The Process of any of the preceding processes, wherein the second premix is transferred by vacuum to the mixer or mix tank.
1.17 The Process of any of the preceding processes, wherein the third premix comprises an anionic surfactant, and wherein the anionic surfactant is selected from water-soluble salts of higher fatty acid monoglyceride monosulfates, such as the sodium salt of the monosulfated monoglyceride of hydrogenated coconut oil fatty acids such as sodium N- methyl N-cocoyl taurate, sodium cocomo-glyceride sulfate; higher alkyl sulfates, such as sodium lauryl sulfate; higher alkyl-ether sulfates, e.g., of formula $CH_3(CH_2)_mCH_2(OCH_2CH_2)_nOSO_3X$, wherein m is 6-16, e.g., 10, n is 1-6, e.g., 2, 3 or 4, and X is Na or, for example sodium laureth-2 sulfate $(CH_3(CH_2)_{10}CH_2(OCH_2CH_2)_2OSO_3Na)$; higher alkyl aryl sulfonates such as sodium dodecyl benzene sulfonate (sodium lauryl benzene sulfonate); higher alkyl sulfoacetates, such as sodium lauryl sulfoacetate (dodecyl sodium sulfoacetate), higher fatty acid esters of 1,2 dihydroxy propane sulfonate, sulfocolaurate (N-2-ethyl laurate potassium sulfoacetamide) and sodium lauryl sarcosinate.

1.18 The Process of 1.17, wherein the anionic surfactant is sodium lauryl sulfate.
1.19 The Process of any of the preceding processes, wherein the process comprises packaging the final composition to produce a packaged oral care composition in a container.
1.20 The Process of any of the preceding processes, wherein the container that holds the packaged oral care composition has reduced bloating relative to a container that holds an oral care composition that was not produced by a premix with a pH adjusting agent (e.g., sodium carbonate).
1.21 The Process of any of the preceding processes, wherein the chronological order or sequence of the process comprises or consists of:
  a.) First, forming a first aqueous premix comprising water, a pH adjusting agent (e.g., sodium carbonate) and a zinc salt (e.g., zinc citrate); forming a second premix comprising one or more humectants (e.g., glycerin and xanthan gum); forming a third aqueous premix comprising water and an anionic surfactant (e.g., sodium lauryl sulfate), wherein the premixes are formed simultaneously or in close chronological proximity to one another;
  b.) Second, transferring the second premix to a separate tank (e.g., gel tank);
  c.) Third, transferring the first, second, and third premixes to a separate mixer or a mix tank;
  d.) Fourth, homogenizing and forming the first, second, and third premixes into a final composition within the mixer or mix tank, wherein the final composition comprises all of the above premixes.
1.22 The Process of any of the preceding processes, wherein the process comprises or consists of:
  a. forming a first aqueous premix comprising water, sodium carbonate, and zinc citrate;
  b. forming a second premix comprising glycerin and xanthan gum;
  c. forming a third aqueous premix comprising water and sodium lauryl sulfate;
  d. transferring the second premix to a separate gel tank;
  e. transferring the first, second, and third premixes to a separate mixer or a mix tank;
  f. homogenizing and forming the first, second, and third premixes into a final composition within the mixer or mix tank, wherein the final composition comprises all of the above premixes, and wherein the mixer or mix tank is first heated to 150° F.-170° F. (e.g., about 160° F.) prior to transfer of any of the premixes.
1.23 The process of 1.21 or 1.22, wherein the sequence of the process is required to be in the order of a.-d. (e.g., Process 1.21) or a.-f. (e.g., Process 1.22).
1.24 The process of any of the preceding processes, wherein an effective amount sodium carbonate is first to added to a first aqueous premix comprising aqueous premix comprising water, sodium carbonate, and zinc citrate, and wherein the amount of sodium carbonate is effective neutralize any carbonic acid formed during the premix step.
1.25 The process of any of the preceding processes, wherein the mixer or mix tank is made from: stainless steel, plastic, or glass vessels.
1.26 The process of any of the preceding processes wherein "sodium carbonate" is a hydrate of sodium carbonate selected from: sodium carbonate decahydrate (natron), $Na_2CO_3.10H_2O$ (e.g., which readily effloresces to form the monohydrate), sodium carbonate heptahydrate, $Na_2CO_3 \cdot 7H_2O$, and sodium carbonate monohydrate (thermonatrite), $Na_2CO_3$—$H_2O$.

1.27 The process of any of Process 1.0-1.25, wherein "sodium carbonate" is anhydrous sodium carbonate, also known as calcined soda.

In one aspect, the Process of 1.0 et seq., comprises a mixing process which includes the addition of premix components into a mixer or mix tank. The mix tank provides the means for preparing a slurry of the liquid and solid components of the mix. In certain aspects, the mixer or mix tank is heated prior to including the components of one or more premixes. In one aspect, liquids can be added directly to the mix tank, or could be added through a high energy dispersion device, such as an eductor, pump or vacuum, allowing powders to be added concurrently with the liquids. In one aspect, after the main liquids (typically humectants, water, pH adjuster, and potentially flavor and emulsifier/surfactant) are added to the tank the powders or solids can be added to the mix tank. In certain aspects, powder or solids can be added using an eductor, so as to maximize the dispersion during the addition, which minimizes the total processing time.

In one aspect, after all the materials and/or premixes are combined and formed together, the batch or final composition can be mixed or homogenized for a time to deliver homogeneity. In one aspect, mixing can occur under vacuum, for example by using a vacuum pump, or under atmospheric conditions.

In certain aspects, the Process 1.0 et seq, comprises incorporating surfactants within the stream by in line mixing technology, e.g., through the use of static mixers. In certain aspects, most of the surfactant is added after the inline deaeration device so as to maximize efficiencies of the inline deaeration process. Static mixers are well known in the art and are generally in the form of a series of repeating or random, interlocking plates and, or fins. Another type of mixer is that may be used is a dynamic mixer. Additionally, surge tanks may be used to provide more constant flow for materials combined by the process described and claimed herein.

In certain aspects of Process 1.0 et seq, the choice of mixer can be influenced by the phase structure of the resultant composition and optimizing the pressure drop across the system, which is influenced by the rate of hydration. For example, for mixing some materials which are used to produce an isotropic composition, a static mixer is sufficient. For mixing other materials to produce a lamellar composition, greater agitation can be used to build the viscosity of the resultant composition. Therefore, a dynamic mixing system may be appropriate, such as a high shear mill. A dynamic mixing system as used herein is inclusive of the batch and continuous stir systems which use an impeller, jet mixing nozzle, a recirculating loop, gas percolation, rotating or fixed screen or similar means of agitation to combine materials therein.

In certain aspects, Process 1.0 et seq, can utilize one or more additional processing methods and the products produced by employing multiple processing methods that can then be discharged into a common container, thereby forming for example, a product having multiple layers, phases, patterns etc. Such layers, phases and/or patterns may or may not mix in the container to form a homogeneous product. In certain aspects of Process 1.0 et seq a first phase of a product may be in a separate location from the process to produce a second or multiple phases for filling the container with the final multi-phase composition, e.g., a dentifrice with a paste phase and a gel phase.

In one aspect, the Process 1.0 et seq comprises the use of a filling line to fill containers with a first phase, a second phase, combined phase and/or a multiphase composition. In one other aspect, where the composition is intended to be combined with another composition to form a multiphase product it may be filled into containers in many ways. For example, one could fill containers by combining toothpaste-tube filling technology with a spinning stage design. In certain aspects of Process 1.0 et seq, allows two or more compositions to be filled in a spiral configuration into a single container using at least two nozzles to fill a container, which is placed on a rotating stage and spun as the composition is introduced into the container.

In yet another aspect, the invention contemplates a Composition (2.0) made or produced by any of the Process 1.0 et seq. In a further aspect, Composition 2.0 can comprise any of the following:

2.1 The Composition of 2.0, wherein the composition further comprises an abrasive or particulate source.

2.2 The Composition of 2.1, wherein the abrasive or particulate comprises one or more selected from sodium bicarbonate, calcium phosphate (e.g., dicalcium phosphate dihydrate), calcium sulfate, calcium carbonate (e.g., precipitated calcium carbonate) (e.g., natural calcium carbonate), calcium pyrophosphate, silica (e.g., hydrated silica) (e.g., precipitated silica), iron oxide, aluminum oxide, perlite, plastic particles, e.g., polyethylene, and combinations thereof.

2.3 Composition of 2.2, wherein the abrasive or particulate comprises one or more types of silica.

2.4 Composition 2.3, wherein at least one type of silica is a synthetic abrasive silica. (e.g., 1%-25% by wt.) (e.g., 8%-25% by wt.) (e.g., about 12% by wt.)

2.5 Composition of 2.4, wherein at least one type of silica has an average particle size ranging from 2.5 microns to 12 microns.

2.6 Any of the preceding compositions, wherein at least one type of silica is a small particle silica having a median particle size (d50) of 1-5 microns (e.g., 3-4 microns) (e.g., about 5 wt. % Sorbosil AC43 from Ineos Silicas, Warrington, United Kingdom).

2.7 Any of the preceding compositions, comprising 15-30 wt % of total silica in the composition.

2.8 Any of the preceding compositions, wherein at least one type of silica is small particle silica (e.g., having a median particle size (d50) of 3-4 microns) and wherein the small particle silica is about 10 wt. % of the oral care composition.

2.9 Any of the preceding compositions comprising silica wherein the silica is used as a thickening agent, e.g., particle silica.

2.10 The composition according to 2.2, wherein the abrasive or particulate is natural calcium carbonate (e.g., limestone)

2.11 Any of the preceding compositions, wherein the composition further comprises a zinc ion source.

2.12 A composition according to 2.11, wherein the zinc ion source comprises a zinc salt selected from the group consisting of: zinc citrate, zinc oxide, zinc phosphate, zinc lactate, zinc sulfate, zinc silicate, zinc gluconate and combinations thereof (e.g., zinc citrate and zinc oxide) (e.g., zinc phosphate) (e.g., zinc lactate).

2.13 A composition of 2.12, wherein the zinc ion source is zinc citrate.

2.14 Any of the preceding compositions, wherein the composition comprises a stannous ion source.

2.15 A composition according to 2.14, wherein the stannous ion source is selected from the group consisting of: stannous fluoride, other stannous halides such as stannous chloride dihydrate, stannous pyrophosphate, organic stannous carboxylate salts such as stannous formate, acetate, gluconate, lactate, tartrate, oxalate, malonate and citrate, stannous ethylene glyoxide, or a mixture thereof.

2.16 A composition according to 2.15, wherein the stannous ion source is stannous fluoride.

2.17 Any of the preceding compositions, wherein the composition comprises a copolymer.

2.18 The composition of 2.17, wherein the copolymer is a PVM/MA copolymer.

2.19 The composition of 2.18, wherein the PVM/MA copolymer comprises a 1:4 to 4:1 copolymer of maleic anhydride or acid with a further polymerizable ethylenically unsaturated monomer; for example 1:4 to 4:1, e.g. about 1:1.

2.20 Any of the preceding compositions, wherein the further polymerizable ethylenically unsaturated monomer comprises methyl vinyl ether (methoxyethylene).

2.21 Any of the preceding compositions, wherein the PVM/MA copolymer comprises a copolymer of methyl vinyl ether/maleic anhydride, wherein the anhydride is hydrolyzed following copolymerization to provide the corresponding acid.

2.22 Any of the preceding compositions, wherein the PVM/MA copolymer comprises a GANTREZ® polymer (e.g., GANTREZ® S-97 polymer)

2.23 Any of the preceding compositions wherein the pH is between 7.5 and 10.5. e.g., about 7.5 or about 8.0.

2.24 Any of the preceding compositions further comprising a fluoride ion source.

2.25 The composition of 2.24, wherein the fluoride ion source is selected from the group consisting of stannous fluoride, sodium fluoride, potassium fluoride, sodium monofluorophosphate, sodium fluorosilicate, ammonium fluorosilicate, amine fluoride, ammonium fluoride, and combinations thereof.

2.26 The composition of 2.25, wherein the fluoride ion source is sodium fluoride and/or sodium monofluorophosphate.

2.27 Any of the preceding compositions wherein the polyphosphate is sodium tripolyphosphate (STPP).

2.28 The composition of 2.27, wherein the sodium tripolyphosphate is from 0.5-5.0 wt % (e.g., about 3.0 wt %).

2.29 Any of the preceding compositions further comprising an effective amount of one or more alkali phosphate salts, e.g., sodium, potassium or calcium salts, e.g., selected from alkali dibasic phosphate and alkali pyrophosphate salts, e.g., alkali phosphate salts selected from sodium phosphate dibasic, potassium phosphate dibasic, dicalcium phosphate dihydrate, calcium pyrophosphate, tetrasodium pyrophosphate, tetrapotassium pyrophosphate, disodium hydrogenorthophosphate, monosodium phosphate, pentapotassium triphosphate and mixtures of any of two or more of these, e.g., in an amount of 1-20%, e.g., 2-8%, e.g., ca. 5%>, by weight of the composition.

2.30 Any of the preceding compositions, wherein the orally acceptable vehicle comprises one or more of water, a thickener, a buffer, a humectant, a surfactant, a sweetener, a pigment, a dye, an anti-caries agent, an anti-bacterial, a whitening agent, a desensitizing agent, a vitamin, a preservative, and mixtures thereof.

2.31 Any of the preceding compositions further comprising an anionic surfactant, wherein the anionic surfactant is in an amount of from 0.5-5% by wt., e.g., 1-2% by weight, selected from water-soluble salts of higher fatty acid monoglyceride mono sulfates, (e.g., sodium N- methyl N-cocoyl taurate), sodium cocomo-glyceride sulfate; higher alkyl sulfates, (e.g., sodium lauryl sulfate); higher alkyl-ether sulfates (e.g., of formula $CH_3(CH_2)_mCH_2(OCH_2CH_2)_nOSO_3X$, wherein m is 6-16, e.g., 10, n is 1-6, e.g., 2, 3 or 4, and X is Na) or (e.g., sodium laureth-2 sulfate $(CH_3(CH_2)_{10}CH_2(OCH_2CH_2)_2OSO_3Na)$; higher alkyl aryl sulfonates (e.g., sodium dodecyl benzene sulfonate, sodium lauryl benzene sulfonate); higher alkyl sulfoacetates (e.g., sodium lauryl sulfoacetate; dodecyl sodium sulfoacetate), higher fatty acid esters of 1,2 dihydroxy propane sulfonate, sulfocolaurate (e.g., N-2-ethyl laurate potassium sulfoacetamide) and sodium lauryl sarcosinate, and mixtures thereof.

2.32 Any of the preceding compositions, wherein the anionic surfactant is sodium lauryl sulfate (e.g., from 1.0-2.0% by wt.) (e.g., from 1.0-1.5% by wt.) (e.g., about 1.2% by wt.).

2.33 Any of the preceding composition comprising a humectant.

2.34 The composition of 2.33, wherein the humectant comprises one or more selected from glycerin, sorbitol, xylitol, propylene glycol, polyols and combinations thereof.

2.35 A composition of 2.34, wherein the humectant comprises glycerin, wherein the glycerin is in a total amount of 5-20% by wt. (e.g., about 10% by wt.).

2.36 A composition of any of 2.33-2.35 comprising xylitol (e.g., in a total amount of 5-20% by wt.) (e.g., about 10% by wt.).

2.37 Any of the preceding compositions comprising polymer films.

2.38 Any of the preceding compositions comprising a flavoring agent, fragrance and/or coloring.

2.39 The composition of 2.38, wherein the flavoring agent is sodium saccharin, sucralose, or a mixture thereof.

2.40 Any of the preceding compositions comprising from 5%-40%, e.g., 10%-35%, e.g., about 10%, about 12%, about 14%, about 15%, about 18%, about 20%, about 25%, about 30%, and about 35% water.

2.41 Any of the preceding compositions comprising an additional antibacterial agent selected from halogenated diphenyl ether (e.g. triclosan), herbal extracts and essential oils (e.g., rosemary extract, tea extract, magnolia extract, thymol, menthol, eucalyptol, geraniol, carvacrol, citral, hinokitol, catechol, methyl salicylate, epigallocatechin gallate, epigallocatechin, gallic acid, miswak extract, sea-buckthorn extract), bisguanide antiseptics (e.g., chlorhexidine, alexidine or octenidine), quaternary ammonium compounds (e.g., cetylpyridinium chloride (CPC), benzalkonium chloride, tetradecylpyridinium chloride (TPC), N-tetradecyl-4-ethylpyridinium chloride (TDEPC)), phenolic antiseptics, hexetidine, octenidine, sanguinarine, povidone iodine, delmopinol, salifluor, metal ions (e.g., zinc salts, for example, Zinc Chloride, Zinc Lactate, Zinc Sulfate, stannous salts, copper salts, iron salts), sanguinarine, propolis and oxygenating agents (e.g., hydrogen peroxide, buffered sodium peroxyborate or peroxycarbonate), phthalic acid and its salts, monoperthalic acid and its salts and esters, ascorbyl stearate, oleoyl sarcosine, alkyl sulfate, dioctyl sulfosuccinate, salicylanilide, domiphen bromide, delmopinol, octapinol and other piperidino derivatives, nicin preparations, chlorite salts; and mixtures of any of the foregoing.

2.42 Any of the preceding compositions comprising an antioxidant, e.g., selected from the group consisting of Co-enzyme Q10, PQQ, Vitamin C, Vitamin E, Vitamin A, BHT, anethole-dithiothione, and mixtures thereof.

2.43 Any of the preceding compositions comprising a whitening agent.

2.44 The composition of 2.43, wherein the whitening agent is titanium dioxide.

2.45 Any of the preceding compositions comprising a whitening agent selected from a whitening active selected from the group consisting of peroxides, metal chlorites, perborates, percarbonates, peroxyacids, hypochlorites, and combinations thereof.

2.46 Any of the preceding compositions further comprising hydrogen peroxide or a hydrogen peroxide source, e.g., urea peroxide or a peroxide salt or complex (e.g., such as peroxyphosphate, peroxycarbonate, perborate, peroxysilicate, or persulphate salts; for example calcium peroxyphosphate, sodium perborate, sodium carbonate peroxide, sodium peroxyphosphate, and potassium persulfate), or hydrogen peroxide polymer complexes such as hydrogen peroxide-polyvinyl pyrrolidone polymer complexes.

2.47 Any of the preceding compositions further comprising an agent that interferes with or prevents bacterial attachment, e.g., ELA or chitosan.

2.48 Any of the preceding compositions comprising a pH adjusting agent.

2.49 The composition of 2.48, wherein the pH adjusting agent is sodium carbonate (e.g., from 0.1%-0.5% by wt. of the total composition) (e.g., about 0.25% by wt. of the total composition).

2.50 Any of the preceding compositions that is obtained, or obtainable, by any of the Process 1.0, et seq.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION

As used herein, an "oral care composition" refers to a composition for which the intended use includes oral care, oral hygiene, and/or oral appearance, or for which the intended method of use comprises administration to the oral cavity, and refers to compositions that are palatable and safe for topical administration to the oral cavity, and for providing a benefit to the teeth and/or oral cavity. The term "oral care composition" thus specifically excludes compositions which are highly toxic, unpalatable, or otherwise unsuitable for administration to the oral cavity. In some embodiments, an oral care composition is not intentionally swallowed, but is rather retained in the oral cavity for a time sufficient to affect the intended utility. The oral care compositions as disclosed herein may be used in nonhuman mammals such as companion animals (e.g., dogs and cats), as well as by humans. In some embodiments, the oral care compositions as disclosed herein are used by humans. Oral care compositions include, for example, dentifrice and mouthwash. In some embodiments, the disclosure provides mouthwash formulations.

As used herein, the term "pH adjusting agent" means an agent that is added during a process, or to a composition or premix, that reduces or prevents the generation of excess gas (e.g., carbon dioxide) that causes bloating or breakage of the container housing the formulation.

As used herein, the term "dentifrice" means paste, gel, or liquid formulations unless otherwise specified. The dentifrice composition can be in any desired form such as deep striped, surface striped, multi-layered, having the gel surrounding the paste, or any combination thereof. Alternatively, the oral composition may be dual phase dispensed from a separated compartment dispenser.

As used herein, "mixer" or "mix tank" can be used interchangeably. In one aspect the terms refer to a machine or container that is used to blend various components together.

As used herein, "sodium carbonate" and "soda ash" can be used interchangeably. Both terms refer to the inorganic compound with the formula $Na_2CO_3$. In one aspect, "sodium carbonate" refers to a hydrate of sodium carbonate selected from: sodium carbonate decahydrate (natron), $Na_2CO_3.10H_2O$ (e.g., which readily effloresces to form the monohydrate), sodium carbonate heptahydrate, $Na_2CO_3.7H_2O$, and sodium carbonate monohydrate (thermonatrite), $Na_2CO_3.H_2O$. In another aspect, "sodium carbonate" refers to anhydrous sodium carbonate, also known as calcined soda.

Examples of some of the components that can be used to make dentifrice according to the methods of the present invention are listed below:

Amino Acids

In certain embodiments, the process described herein (e.g., any of Process 1.0 et seq) and/or the oral care composition (e.g., any of Composition 2.0 et seq) may further include the incorporation of one or more basic amino acids. The basic amino acids which can be used in the compositions and methods of the invention include not only naturally occurring basic amino acids, such as arginine, lysine, and histidine, but also any basic amino acids having a carboxyl group and an amino group in the molecule, which are water-soluble and provide an aqueous solution with a pH of 7 or greater.

Accordingly, basic amino acids include, but are not limited to, arginine, lysine, serine, citrullene, ornithine, creatine, histidine, diaminobutanoic acid, diaminoproprionic acid, salts thereof or combinations thereof. In a particular embodiment, the basic amino acids are selected from arginine, citrullene, and ornithine.

In certain embodiments, the basic amino acid is arginine, for example, L-arginine, or a salt thereof.

In another aspect, in addition to the basic amino acid included in the formulation, the process described herein (e.g., any of Process 1.0 et seq) and/or the oral care composition of the invention (e.g., Compositions 2.0 et seq) can further include a neutral amino acid (either alone or in combination with a basic amino acid), which can include, but are not limited to, one or more neutral amino acids selected from the group consisting of alanine, aminobutyrate, asparagine, cysteine, cystine, glutamine, glycine, hydroxyproline, isoleucine, leucine, methionine, phenylalanine, proline, serine, taurine, threonine, tryptophan, tyrosine, valine, and combinations thereof.

The compositions of the invention are intended for topical use in the mouth and so salts for use in the present invention should be safe for such use, in the amounts and concentrations provided. Suitable salts include salts known in the art to be pharmaceutically acceptable salts are generally considered to be physiologically acceptable in the amounts and concentrations provided. Physiologically acceptable salts include those derived from pharmaceutically acceptable inorganic or organic acids or bases, for example acid addition salts formed by acids which form a physiological acceptable anion, e.g., hydrochloride or bromide salt, and base addition salts formed by bases which form a physiologically acceptable cation, for example those derived from alkali metals such as potassium and sodium or alkaline earth metals such as calcium and magnesium. Physiologically acceptable salts may be obtained using standard procedures known in the art, for example, by reacting a sufficiently basic compound such as an amine with a suitable acid affording a physiologically acceptable anion.

Fluoride Ion Source

In certain embodiments, the process described herein (e.g., any of Process 1.0 et seq) and/or the oral care composition (e.g., any of Composition 2.0 et seq) may further include one or more fluoride ion sources, e.g., soluble fluoride salts. A wide variety of fluoride ion-yielding materials can be employed as sources of soluble fluoride in the present compositions. Examples of suitable fluoride ion-yielding materials are found in U.S. Pat. No. 3,535,421, to Briner et al.; U.S. Pat. No. 4,885,155, to Parran, Jr. et al. and U.S. Pat. No. 3,678,154, to Widder et al., each of which are incorporated herein by reference. Representative fluoride ion sources used with the present invention (e.g., Composition 1.0 et seq.) include, but are not limited to, stannous fluoride, sodium fluoride, potassium fluoride, sodium monofluorophosphate, sodium fluorosilicate, ammonium fluorosilicate, amine fluoride, ammonium fluoride, and combinations thereof. In certain embodiments the fluoride ion source includes stannous fluoride, sodium fluoride, sodium monofluorophosphate as well as mixtures thereof. Where the formulation comprises calcium salts, the fluoride salts are preferably salts wherein the fluoride is covalently bound to another atom, e.g., as in sodium monofluorophosphate, rather than merely ionically bound, e.g., as in sodium fluoride.

Surfactants

In certain embodiments, the process described herein (e.g., any of Process 1.0 et seq) and/or the oral care composition (e.g., any of Composition 2.0 et seq) can include anionic surfactants, for example, water-soluble salts of higher fatty acid monoglyceride monosulfates, such as the sodium salt of the monosulfated monoglyceride of hydrogenated coconut oil fatty acids such as sodium N- methyl N-cocoyl taurate, sodium cocomo-glyceride sulfate; higher alkyl sulfates, such as sodium lauryl sulfate; higher alkyl-ether sulfates, e.g., of formula $CH_3(CH_2)_mCH_2(OCH_2CH_2)_nOSO_3X$, wherein m is 6-16, e.g., 10, n is 1-6, e.g., 2, 3 or 4, and X is Na or, for example sodium laureth-2 sulfate $(CH_3(CH_2)_{10}CH_2(OCH_2CH_2)_2OSO_3Na)$; higher alkyl aryl sulfonates such as sodium dodecyl benzene sulfonate (sodium lauryl benzene sulfonate); higher alkyl sulfoacetates, such as sodium lauryl sulfoacetate (dodecyl sodium sulfoacetate), higher fatty acid esters of 1,2 dihydroxy propane sulfonate, sulfocolaurate (N-2-ethyl laurate potassium sulfoacetamide) and sodium lauryl sarcosinate. By "higher alkyl" is meant, e.g., $C_{6-30}$ alkyl. In particular embodiments, the anionic surfactant (where present) is selected from sodium lauryl sulfate and sodium ether lauryl sulfate. When present, the anionic surfactant is present in an amount which is effective, e.g., >0.001% by weight of the formulation, but not at a concentration which would be irritating to the oral tissue, e.g., 1%, and optimal concentrations depend on the particular formulation and the particular surfactant. In one embodiment, the anionic surfactant is present at from 0.03% to 5% by weight, e.g., 1.5%.

In another embodiment, cationic surfactants useful in the present invention can be broadly defined as derivatives of aliphatic quaternary ammonium compounds having one long alkyl chain containing 8 to 18 carbon atoms such as lauryl trimethylammonium chloride, cetyl pyridinium chloride, cetyl trimethylammonium bromide, di-isobutylphenoxyethyldimethylbenzylammonium chloride, coconut alkyltrimethylammonium nitrite, cetyl pyridinium fluoride, and mixtures thereof. Illustrative cationic surfactants are the quaternary ammonium fluorides described in U.S. Pat. No. 3,535,421, to Briner et al., herein incorporated by reference. Certain cationic surfactants can also act as germicides in the compositions.

Illustrative nonionic surfactants of Process 1.0, et seq., or Composition 2.0 et seq., that can be used in the compositions of the invention can be broadly defined as compounds produced by the condensation of alkylene oxide groups (hydrophilic in nature) with an organic hydrophobic compound which may be aliphatic or alkylaromatic in nature. Examples of suitable nonionic surfactants include, but are not limited to, the Pluronics, polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides and mixtures of such materials. In a particular embodiment, the composition of the invention comprises a nonionic surfactant selected from polaxamers (e.g., polaxamer 407), polysorbates (e.g., polysorbate 20), polyoxyl hydrogenated castor oils (e.g., polyoxyl 40 hydrogenated castor oil), and mixtures thereof.

In still another embodiment amphoteric surfactants can be used. Suitable amphoteric surfactants, without limitation, are derivatives of $C_{8-20}$ aliphatic secondary and tertiary amines having an anionic group such as carboxylate, sulfate, sulfonate, phosphate or phosphonate. A suitable example is cocoamidopropyl betaine. One or more surfactants are optionally present in a total amount of 0.01 weight % to 10 weight %, for example, from 0.05 weight % to 5 weight % or from 0.1 weight % to 2 weight % by total weight of the composition.

The surfactant or mixtures of compatible surfactants can be present in the compositions of the present invention in 0.1% to 5%, in another embodiment 0.3% to 3% and in another embodiment 0.5% to 2% by weight of the total composition.

Flavoring Agents

In certain embodiments, the process described herein (e.g., any of Process 1.0 et seq) and/or the oral care composition (e.g., any of Composition 2.0 et seq) may also include a flavoring agent. Flavoring agents which are used in the practice of the present invention include, but are not limited to, essential oils and various flavoring aldehydes, esters, alcohols, and similar materials, as well as sweeteners such as sodium saccharin. Examples of the essential oils include oils of spearmint, peppermint, wintergreen, sassafras, clove, sage, eucalyptus, marjoram, cinnamon, lemon, lime, grapefruit, and orange. Also useful are such chemicals as menthol, carvone, and anethole. Certain embodiments employ the oils of peppermint and spearmint.

The flavoring agent is incorporated in the oral composition at a concentration of 0.01 to 1% by weight.

Chelating and Anti-Calculus Agents

In certain embodiments, the process described herein (e.g., any of Process 1.0 et seq) and/or the oral care composition (e.g., any of Composition 2.0 et seq) also may include one or more chelating agents able to complex calcium found in the cell walls of the bacteria. Binding of this calcium weakens the bacterial cell wall and augments bacterial lysis.

Another group of agents suitable for use as chelating or anti-calculus agents in the present invention are the soluble pyrophosphates. The pyrophosphate salts used in the present compositions can be any of the alkali metal pyrophosphate salts. In certain embodiments, salts include tetra alkali metal pyrophosphate, dialkali metal diacid pyrophosphate, trialkali metal monoacid pyrophosphate and mixtures thereof, wherein the alkali metals are sodium or potassium. The salts are useful in both their hydrated and unhydrated forms. An effective amount of pyrophosphate salt useful in the present composition is generally enough to provide at least 0.5 wt. % pyrophosphate ions, 0.9-3 wt. %. The pyrophosphates also contribute to preservation of the compositions by lowering water activity.

Polymers

In certain embodiments, the process described herein (e.g., any of Process 1.0 et seq) and/or the oral care composition (e.g., any of Composition 2.0 et seq) also optionally include one or more polymers, such as polyethylene glycols, polyvinyl methyl ether maleic acid copolymers, polysaccharides (e.g., cellulose derivatives, for example carboxymethyl cellulose, or polysaccharide gums, for example xanthan gum or carrageenan gum). Acidic polymers, for example polyacrylate gels, may be provided in the form of their free acids or partially or fully neutralized water soluble alkali metal (e.g., potassium and sodium) or ammonium salts. Certain embodiments include 1:4 to 4:1 copolymers of maleic anhydride or acid with another polymerizable ethylenically unsaturated monomer, for example, methyl vinyl ether (methoxyethylene) having a molecular weight (M.W.) of about 30,000 to about 1,000,000. These copolymers are available for example as Gantrez AN 139(M.W. 500,000), AN 1 19 (M.W. 250,000) and S-97 Pharmaceutical Grade (M.W. 70,000), of GAF Chemicals Corporation.

Other operative polymers include those such as the 1:1 copolymers of maleic anhydride with ethyl acrylate, hydroxyethyl methacrylate, N-vinyl-2-pyrollidone, or ethylene, the latter being available for example as Monsanto EMA No. 1 103, M.W. 10,000 and EMA Grade 61, and 1:1 copolymers of acrylic acid with methyl or hydroxyethyl methacrylate, methyl or ethyl acrylate, isobutyl vinyl ether or N-vinyl-2-pyrrolidone.

Suitable generally, are polymerized olefinically or ethylenically unsaturated carboxylic acids containing an activated carbon-to-carbon olefinic double bond and at least one carboxyl group, that is, an acid containing an olefinic double bond which readily functions in polymerization because of its presence in the monomer molecule either in the alphabeta position with respect to a carboxyl group or as part of a terminal methylene grouping. Illustrative of such acids are acrylic, methacrylic, ethacrylic, alpha-chloroacrylic, crotonic, beta-acryloxy propionic, sorbic, alpha-chlorsorbic, cinnamic, beta-styrylacrylic, muconic, itaconic, citraconic, mesaconic, glutaconic, aconitic, alpha-phenylacrylic, 2-benzyl acrylic, 2-cyclohexylacrylic, angelic, umbellic, fumaric, maleic acids and anhydrides. Other different olefinic monomers copolymerizable with such carboxylic monomers include vinylacetate, vinyl chloride, dimethyl maleate and the like. Copolymers contain sufficient carboxylic salt groups for water-solubility.

A further class of polymeric agents includes a composition containing homopolymers of substituted acrylamides and/or homopolymers of unsaturated sulfonic acids and salts thereof, in particular where polymers are based on unsaturated sulfonic acids selected from acrylamidoalykane sulfonic acids such as 2-acrylamide 2 methylpropane sulfonic acid having a molecular weight of about 1,000 to about 2,000,000, described in U.S. Pat. No. 4,842,847, Jun. 27, 1989 to Zahid, incorporated herein by reference.

Another useful class of polymeric agents includes polyamino acids, particularly those containing proportions of anionic surface-active amino acids such as aspartic acid, glutamic acid and phosphoserine, as disclosed in U.S. Pat. No. 4,866,161 Sikes et al., incorporated herein by reference.

In preparing oral care compositions, it is sometimes necessary to add some thickening material to provide a desirable consistency or to stabilize or enhance the performance of the formulation. In certain embodiments, the thickening agents are carboxyvinyl polymers, carrageenan, hydroxyethyl cellulose and water soluble salts of cellulose ethers such as sodium carboxymethyl cellulose and sodium carboxymethyl hydroxyethyl cellulose. Natural gums such as karaya, gum arabic, and gum tragacanth can also be incorporated. Colloidal magnesium aluminum silicate or finely divided silica can be used as component of the thickening composition to further improve the composition's texture. In certain embodiments, thickening agents in an amount of about 0.5% to about 5.0% by weight of the total composition are used.

Abrasives

In certain embodiments, the process described herein (e.g., any of Process 1.0 et seq) and/or the oral care composition (e.g., any of Composition 2.0 et seq) can include one or more abrasives. Natural calcium carbonate is found in rocks such as chalk, limestone, marble and travertine. It is also the principle component of egg shells and the shells of mollusks. The natural calcium carbonate abrasive of the invention is typically a finely ground limestone which may optionally be refined or partially refined to remove impurities. For use in the present invention, the material has an average particle size of less than 10 microns, e.g., 3-7 microns, e.g., about 5.5 microns. For example, a small particle silica may have an average particle size (D50) of 2.5-4.5 microns. Because natural calcium carbonate may contain a high proportion of relatively large particles of not carefully controlled, which may unacceptably increase the abrasivity, preferably no more than 0.01%, preferably no more than 0.004% by weight of particles would not pass through a 325 mesh. The material has strong crystal structure, and is thus much harder and more abrasive than precipitated calcium carbonate. The tap density for the natural calcium carbonate is for example between 1 and 1.5 g/cc, e.g., about 1.2 for example about 1.19 g/cc. There are different polymorphs of natural calcium carbonate, e.g., calcite, aragonite and vaterite, calcite being preferred for purposes of this invention. An example of a commercially available product suitable for use in the present invention includes Vicron® 25-11 FG from GMZ.

Precipitated calcium carbonate is generally made by calcining limestone, to make calcium oxide (lime), which can then be converted back to calcium carbonate by reaction with carbon dioxide in water. Precipitated calcium carbonate has a different crystal structure from natural calcium carbonate. It is generally more friable and more porous, thus having lower abrasivity and higher water absorption. For use in the present invention, the particles are small, e.g., having an average particle size of 1-5 microns, and e.g., no more than 0.1%, preferably no more than 0.05% by weight of particles which would not pass through a 325 mesh. The particles may for example have a D50 of 3-6 microns, for example 3.8=4.9, e.g., about 4.3; a D50 of 1-4 microns, e.g., 2.2-2.6 microns, e.g., about 2.4 microns, and a D10 of 1-2 microns, e.g., 1.2-1.4, e.g., about 1.3 microns. The particles have relatively high water absorption, e.g., at least 25 g/100 g, e.g., 30-70 g/100 g. Examples of commercially available products suitable for use in the present invention include, for example, Carbolag® 15 Plus from Lagos Industria Quimica.

In certain embodiments the process or composition of the disclosure may comprise additional calcium-containing abrasives, for example calcium phosphate abrasive, e.g., tricalcium phosphate ($Ca_3(PO_4)_2$), hydroxyapatite ($Ca_{10}(PO_4)_6(OH)_2$), or dicalcium phosphate dihydrate ($CaHPO_4.2H_2O$, also sometimes referred to herein as DiCal) or calcium pyrophosphate, and/or silica abrasives, sodium metaphosphate, potassium metaphosphate, aluminum silicate, calcined alumina, bentonite or other siliceous materials, or combinations thereof. Any silica suitable for oral care compositions may be used, such as precipitated silicas or silica gels. For example synthetic amorphous silica. Silica may also be available as a thickening agent, e.g., particle silica. For example, the silica can also be small particle silica (e.g., Sorbosil AC43 from Ineos Silicas, Warrington, United Kingdom). However the additional abrasives are preferably not present in a type or amount so as to increase the RDA of the dentifrice to levels which could damage sensitive teeth, e.g., greater than 130.

Enzymes

In certain embodiments, the process described herein (e.g., any of Process 1.0 et seq) and/or the oral care composition (e.g., any of Composition 2.0 et seq) may also optionally include one or more enzymes. Useful enzymes include any of the available proteases, glucanohydrolases, endoglycosidases, amylases, mutanases, lipases and mucinases or compatible mixtures thereof In certain embodiments, the enzyme is a protease, dextranase, endoglycosidase and mutanase. In another embodiment, the enzyme is papain, endoglycosidase or a mixture of dextranase and mutanase. Additional enzymes suitable for use in the present invention are disclosed in U.S. Pat. No. 5,000,939 to Dring et al., U.S. Pat. Nos. 4,992,420; 4,355,022; 4,154,815; 4,058,595; 3,991,177; and U.S. Pat. No. 3,696,191 all incorporated herein by reference. An enzyme of a mixture of several compatible enzymes in the current invention constitutes 0.002% to 2.0% in one embodiment or 0.05% to 1.5% in another embodiment or in yet another embodiment 0.1% to 0.5%.

Water

Water can be present in the oral compositions and processes of the invention. Water, employed in the preparation of commercial oral compositions should be deionized and free of organic impurities. Water commonly makes up the balance of the compositions and includes 5% to 45%, e.g., 10% to 20%, e.g., 25-35%, by weight of the oral compositions. This amount of water includes the free water which is added plus that amount which is introduced with other materials such as with sorbitol or silica or any components of the invention. The Karl Fischer method is a one measure of calculating free water.

Humectants

In certain embodiments, the process described herein (e.g., any of Process 1.0 et seq) and/or the oral care composition (e.g., any of Composition 2.0 et seq), it is also desirable to incorporate a humectant to reduce evaporation and also contribute towards preservation by lowering water activity. Certain humectants can also impart desirable sweetness or flavor to the compositions. The humectant, on a pure humectant basis, generally includes 15% to 70% in one embodiment or 30% to 65% in another embodiment by weight of the composition.

Suitable humectants include edible polyhydric alcohols such as glycerine, sorbitol, xylitol, propylene glycol as well as other polyols and mixtures of these humectants. Mixtures of glycerin and sorbitol may be used in certain embodiments as the humectant component of the compositions herein.

The present invention in its method aspect involves applying to the oral cavity a safe and effective amount of the compositions described herein.

The compositions (e.g., Composition 2.0 et seq) according to the invention may be useful to a method to protect the teeth by facilitating repair and remineralization, in particular to reduce or inhibit formation of dental caries, reduce or inhibit demineralization and promote remineralization of the teeth, reduce hypersensitivity of the teeth, and reduce, repair or inhibit early enamel lesions, e.g., as detected by quantitative light-induced fluorescence (QLF) or electronic caries monitor (ECM).

Quantitative Light-induced Fluorescence is a visible light fluorescence that can detect early lesions and longitudinally monitor the progression or regression. Normal teeth fluoresce in visible light; demineralized teeth do not or do so only to a lesser degree. The area of demineralization can be quantified and its progress monitored. Blue laser light is used to make the teeth auto fluoresce. Areas that have lost mineral have lower fluorescence and appear darker in comparison to a sound tooth surface. Software is used to quantify the fluorescence from a white spot or the area/volume associated with the lesion. Generally, subjects with existing white spot lesions are recruited as panelists. The measurements are performed in vivo with real teeth. The lesion area/volume is measured at the beginning of the clinical. The reduction (improvement) in lesion area/volume is measured at the end of 6 months of product use. The data is often reported as a percent improvement versus baseline.

Electrical Caries Monitoring is a technique used to measure mineral content of the tooth based on electrical resistance. Electrical conductance measurement exploits the fact that the fluid-filled tubules exposed upon demineralization and erosion of the enamel conduct electricity. As a tooth loses mineral, it becomes less resistive to electrical current due to increased porosity. An increase in the conductance of the patient's teeth therefore may indicate demineralization. Generally, studies are conducted of root surfaces with an existing lesion. The measurements are performed in vivo with real teeth. Changes in electrical resistance before and after 6-month treatments are made. In addition, a classical caries score for root surfaces is made using a tactile probe.

The hardness is classified on a three-point scale: hard, leathery, or soft. In this type of study, typically the results are reported as electrical resistance (higher number is better) for the ECM measurements and an improvement in hardness of the lesion based on the tactile probe score.

As used throughout, ranges are used as shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls. It is understood that when formulations are described, they may be described in terms of their ingredients, as is common in the art, notwithstanding that these ingredients may react with one another in the actual formulation as it is made, stored and used, and such products are intended to be covered by the formulations described.

The following examples further describe and demonstrate illustrative embodiments within the scope of the present invention. The examples are given solely for illustration and are not to be construed as limitations of this invention as many variations are possible without departing from the spirit and scope thereof. Various modifications of the invention in addition to those shown and described herein should be apparent to those skilled in the art and are intended to fall within the appended claims.

EXAMPLES

Example 1

To test the efficacy of the process described herein using the early addition of a pH adjusting agent (e.g., sodium carbonate), preparation of a three-step process is conducted to examine bloating and/or tube expansion with the addition of a pH adjusting agent such as sodium carbonate.

In one aspect, the steps of the test process comprise the following:

Step 1: Creating premixes

Three separate premixes are created as follows:
- A premix 1 contains zinc citrate and forms with about 7.4% water, by wt. of the total composition and the addition of 0.25% by wt. sodium carbonate and sodium bicarbonate. This is prepared at least one day one prior to all reaction being complete, and ensures carbon dioxide gas is released.
- A premix 2 containing glycerin forms by slowly adding xanthan gum and then mixing;
- A premix 3 containing sodium lauryl sulfate (SLS granules) forms with about 2.8% water, by wt. of the total composition;

Step 2: Preparing contents for Gel Tank:
- Adding water and further amounts of glycerin, mixing. Subsequently adding premix 2 containing xanthan gum, glycerin and xylitol.
- Transferring the contents of the Gel Tank to the mixer and/or mix tank.

Step 3: Preparing final composition in Mixer and/or Mix Tank:
- Heat Mixer to approximately 160° F. Subsequently, contents from the Gel Tank are transferred (e.g., via vacuum) and additional mixing until temperature of the composition is 160° F.
- Limestone is subsequently added.
- Subsequently, premix 1 is added and mixed.
- Subsequently, premix 3 is added and mixed, subsequently flavor and preservative are added, and the total contents are homogenized.

Following completion of the test process, 8 sample formulations are packaged in tube containers. The sample formulations are then subject to a two-week, high temperature, aging study to examine whether any bloating of the tubes occurs. The results after two weeks are as follows:

TABLE 1

| Tube No.: | Initial (mm) | Two Weeks (mm) |
|---|---|---|
| 1 | 18.5 | 19.7 |
| 2 | 18.4 | 17.0 |
| 3 | 18.7 | 15.5 |
| 4 | 18.7 | 16.6 |
| 5 | 18.4 | 19.7 |
| 6 | 18.7 | 17.7 |
| 7 | 18.7 | 14.6 |
| 8 | 17.2 | 16.3 |

The result from the aging study indicate that the amount of tube expansion is within acceptable levels. There is no evidence of any tubes bursting during the aging study.

Average initial measurements taken 40 mm from the bottom crimp of the tube. Measurements are made using standard calipers. Moderate bloating of the tube is considered to be 20 to 25 mm and severe bloating is >25 mm to and including bursting.

However, in a separate aging study similar to the one detailed in Table 1, using samples created from a similar process as described in Example 1, but which did not include the early addition of sodium carbonate during the process, sample formulations are similarly subject to a similar two-week, high temperature, aging study to examine whether any bloating of the tubes occurs. The sample formulations are shown in Table 3 below. The results of the study without the addition of sodium carbonate are listed in Table 1B:

TABLE 1B

| Tube No.: | Initial (mm) | Two Weeks (mm) |
|---|---|---|
| 1 | 23.7 | Burst |
| 2 | 19.7 | Burst |
| 3 | 20.9 | Burst |
| 4 | 23.0 | Burst |
| 5 | 20.0 | Burst |
| 6 | 24.9 | Burst |
| 7 | 21.5 | Burst |

As can be seen in Table 1B, and in contrast to the results in Table 1, the amount of tube expansion is not within acceptable levels. Here, where sodium carbonate was not added, there is evidence that the tested tubes burst during the aging study.

Example 2

Table 2 below describes a representative dentifrice produced by the process described in Example 1, Table 1 above:

TABLE 2

| Materials | Amount (wt %) |
|---|---|
| Water | q.s. |
| Limestone | 40.0 |
| Xylitol | 4.0 |

TABLE 2-continued

| Materials | Amount (wt %) |
|---|---|
| Glycerin | 20.5 |
| Flavor | 1.26 |
| Sodium lauryl sulfate - granules | 1.2 |
| Xanthan gum | 0.6 |
| Zinc citrate | 1.2 |
| Sodium Bicarbonate | 1.0 |
| Sodium Carbonate (Soda Ash) | 0.25 |
| Preservative | 0.5 |
| Thickener | 5.3 |
| Total Components | 100.0 |

Table 3 below describes a representative dentifrice produced by the process described in Example 1, Table 1B above. Note that the contents in Table 1B do not include sodium carbonate (e.g., soda ash):

TABLE 3

| Materials | Amount (wt %) |
|---|---|
| Water | q.s. |
| Limestone | 42.0 |
| Xylitol | 4.0 |
| Glycerin | 20.5 |
| Flavor | 1.26 |
| Sodium lauryl sulfate - granules | 1.2 |
| Xanthan gum | 0.6 |
| Zinc citrate | 1.2 |
| Sodium Bicarbonate | 1.0 |
| Preservative | 0.5 |
| Thickener | 5.5 |
| Total Components | 100.0 |

The present disclosure has been described with reference to exemplary embodiments. Although a limited number of embodiments have been shown and described, it will be appreciated by those skilled in the art that changes may be made in these embodiments without departing from the principles and spirit of the preceding detailed description. It is intended that the present disclosure be construed as including all such modifications and alterations insofar as they come within the scope of the appended claims or the equivalents thereof.

What is claimed is:

1. A process for producing an oral care composition comprising:
   a.) forming a first aqueous premix comprising water, a pH adjusting agent and a zinc salt;
   b.) forming a second premix comprising one or more humectants;
   c.) forming a third aqueous premix comprising water and an anionic surfactant;
   d.) transferring the second premix to a separate tank;
   e.) transferring the first, second, and third premixes to a separate mixer or a mix tank;
   f.) homogenizing and forming the first, second, and third premixes into a final composition within the mixer or mix tank, wherein the final composition comprises all of the above premixes.

2. The process of claim 1, wherein the pH adjusting agent is selected from the group consisting of: sodium bicarbonate, sodium carbonate, disodium hydrogen phosphate and sodium dihydrogen phosphate.

3. The process of claim 1, wherein the pH adjusting agent is sodium carbonate.

4. The process of claim 3, wherein the sodium carbonate is present in an amount from 0.1%-1% by weight of the final composition.

5. The process according to claim 1, wherein the sodium carbonate is present in an amount of about 0.25% by wt weight of the final composition.

6. The process according to claim 1, wherein the zinc salt is selected from zinc chloride, zinc lactate, zinc sulfate, zinc citrate and/or zinc oxide.

7. The process according to claim 6, wherein the zinc salt is zinc citrate.

8. The process according to claim 1, wherein the first aqueous premix is only transferred to the mixer or mix tank after an amount of time that is effective to ensure that the first aqueous premix does not contain any carbon dioxide gas.

9. The process according to claim 1, wherein the first aqueous premix is formed at least 8 hours prior to being transferred to the mixer or mix tank.

10. The process according to claim 1, wherein the mixer or mix tank is heated to at least 130° F. prior to transfer of any of the premixes.

11. The process according to claim 10, wherein the mixer or mix tank is heated to 130° F.-180° F. prior to transfer of either the first or second premixes.

12. The process according to claim 1, wherein an additional humectant is added to the second premix while it is in the tank.

13. The process according to claim 1, wherein the process further comprises forming a third aqueous premix prior to the homogenization step.

14. The process according to claim 1, wherein the second premix is transferred by vacuum to the mixer or mix tank.

15. The process according to claim 1, wherein the third premix comprises an anionic surfactant, and wherein the anionic surfactant is selected from water-soluble salts of higher fatty acid monoglyceride monosulfates, sodium salt of the monosulfated monoglyceride of hydrogenated coconut oil fatty acids, sodium N- methyl N-cocoyl taurate, sodium cocomo-glyceride sulfate; higher alkyl sulfates, sodium lauryl sulfate; higher alkyl-ether sulfates, formula $CH_3(CH_2)_m CH_2(OCH_2CH_2)_n OSO_3X$, wherein m is 6-16, n is 1-6, and X is Na or, sodium laureth-2 sulfate ($CH_3(CH_2)_{10}CH_2(OCH_2CH_2)_2 OSO_3Na$); higher alkyl aryl sulfonates, sodium dodecyl benzene sulfonate (sodium lauryl benzene sulfonate); higher alkyl sulfoacetates, sodium lauryl sulfoacetate (dodecyl sodium sulfoacetate), higher fatty acid esters of 1,2 dihydroxy propane sulfonate, sulfocolaurate (N-2- ethyl laurate potassium sulfoacetamide) and sodium lauryl sarcosinate.

16. The process according to claim 15, wherein the anionic surfactant is sodium lauryl sulfate.

17. The process according to claim 1, wherein the process comprises packaging the final composition to produce a packaged oral care composition in a container.

18. The process according to claim 17, wherein the container that holds the packaged oral care composition has reduced bloating relative to a container that holds an oral care composition that was not produced by a premix with a pH adjusting agent.

19. The process according to claim 1, wherein the chronological order or sequence of the process comprises:
   a.) First, forming a first aqueous premix comprising water, a pH adjusting agent and a zinc salt; forming a second premix comprising one or more humectants; forming a third aqueous premix comprising water and an anionic surfactant, wherein the premixes are formed simultaneously or in close chronological proximity to one another;
b.) Second, transferring the second premix to a separate tank;
c.) Third, transferring the first, second, and third premixes to a separate mixer or a mix tank;
d.) Fourth, homogenizing and forming the first, second, and third premixes into a final composition within the mixer or mix tank, wherein the final composition comprises all of the above premixes.

* * * * *